(12) United States Patent
Gupta et al.

(10) Patent No.: US 11,475,999 B2
(45) Date of Patent: Oct. 18, 2022

(54) FRAMEWORK FOR IN-SILICO DESIGN AND TESTING OF VEHICLES AND FORMULATIONS FOR DELIVERY OF ACTIVE MOLECULES

(71) Applicant: Tata Consultancy Services Limited, Mumbai (IN)

(72) Inventors: Rakesh Gupta, Pune (IN); Aditya Pareek, Pune (IN); Balarama Sridhar Dwadasi, Pune (IN); Beena Rai, Pune (IN); Venkataramana Runkana, Pune (IN)

(73) Assignee: Tata Consultancy Services Limited, Mumbai (IN)

( * ) Notice: Subject to any disclaimer, the term of this patent is extended or adjusted under 35 U.S.C. 154(b) by 307 days.

(21) Appl. No.: 16/880,293

(22) Filed: May 21, 2020

(65) Prior Publication Data
US 2020/0388394 A1 Dec. 10, 2020

(30) Foreign Application Priority Data
May 21, 2019 (IN) .............................. 201921020188

(51) Int. Cl.
*G16H 50/20* (2018.01)
*G16H 70/40* (2018.01)
*G16H 20/10* (2018.01)

(52) U.S. Cl.
CPC ............. *G16H 50/20* (2018.01); *G16H 20/10* (2018.01); *G16H 70/40* (2018.01)

(58) Field of Classification Search
CPC ......... G16H 50/20; G16H 70/40; G16H 20/10
(Continued)

(56) References Cited

U.S. PATENT DOCUMENTS 9,096,877 B2 * 8/2015 Johnson ................ C07K 16/32
9,598,544 B2 * 3/2017 Jiang ....................... C09D 7/62
(Continued)

OTHER PUBLICATIONS

Wishart et al., Drugbank: A Comprehensive Resource For In Silico Drug Discovery And Exploration, Jan. 2006, Nucleic Acids Research, col. 34, Issue Sup. 1, pp. D668-D672 (Year: 2006).*
(Continued)

*Primary Examiner* — Joy Chng
(74) *Attorney, Agent, or Firm* — Finnegan, Henderson, Farabow, Garrett & Dunner, LLP

(57) ABSTRACT

One of the key challenges in healthcare and personal care industries is arriving at an optimum delivery vehicle and formulation which can deliver a specified active molecule to an intended site of action with minimal or no side effects. This disclosure relates to method of designing and testing of a vehicle and formulation for delivery of an active molecule. A plurality of inputs is processed to generate plurality of drug delivery routes. The vehicle associated with formulation is designed based on plurality of parameters associated with the active molecule and the plurality of drug delivery routes. The designed vehicle associated with the formulation on an in-silico model of corresponding chosen drug delivery route is tested to obtain data associated with delivery of the active molecule. The data associated with delivery of the active molecule is reiteratively processed to obtain a desired data associated with the delivery of the active molecule.

12 Claims, 15 Drawing Sheets

(58) Field of Classification Search
USPC .......................................................... 703/11
See application file for complete search history.

(56) References Cited

U.S. PATENT DOCUMENTS

2012/0064142 A1* 3/2012 Pillay .................. A61K 9/5153
977/773
2017/0173262 A1 6/2017 Veltz

OTHER PUBLICATIONS

Anonymous, Formulations, Routes and Dosage Design, Mar. 15, 2010, Pharmaceutical Sciences Encyclopedia, John Wiley & Sons, Inc., DOI: 10.1002/9780470571224.pse131, pp. 1-64 (Year: 2010).*

Shah et al., Recent Advances and Novel Strategies in Pre-Clinical Formulation Development: An Overview, Journal of Controlled Release, Dec. 20, 2011, vol. 156, No. 3, doi: 10.1016/j.jconrel. 2011.07.003, pp. 281-296, Epub Jul. 7, 2011. PMID:21763367. (Year: 2011).*

Wishart et al., Drugbank: A Comprehensive Resource For In Silico Drug Discovery And Exploration, Jan. 2006, Nucleic Acids Research, vol. 34, Issue Sup. 1, pp. D668-D672 (Year: 2006).*

Caccavo et al., Modeling The Drug Release From Hydrogel-Based Matrices, 2015, American Chemical Society, pp. 474-483 (Year: 2015).*

Anonymous, Formulations, Routes and Dosage Design, Mar. 15, 2010, Pharmaceutical Science Encyclopedia, John Wiley & Sons, Inc., DOI: 10.1002/9780470571224.pse131, pp. 1-64 (Year: 2010).*

Mehta et al., Computational Modeling For Formulation Design, Nov. 28, 2018, Drug Discovery Today, vol. 24, No. 3, pp. 781-788, DOI: 10.1016/j.drudis.2018.11.018 (Year: 2018).*

Roy, A. et al. (2017). "In silico methods for design of biological therapeutics," *Methods*, vol. 131; pp. 33-65.

Clancy, C. et al. (Feb. 2016). "Multiscale Modeling in the Clinic: Drug Design and Development," *Annals of Biomedical Engineering*, vol. 44, issue 9; 21 pages.

Ngwuluka, N. (Dec. 2010). "Application of In Situ Polymerization for Design and Development of Oral Drug Delivery Systems," *AAPS PharmSciTech*, vol. 11, No. 4; pp. 1603-1611.

Prokop, A. et al. (Jan. 2002). "Maximizing the In Vivo Efficiency of Gene Transfer by Means of Nonviral Polymeric Gene Delivery Vehicles," *Journal of Pharmaceutical Sciences*, vol. 91, No. 1; 67-76.

Leuenberger, H. et al. (2016). "Impact of the digital revolution on the future of pharmaceutical formulation science," *European Journal of Pharmaceutical Sciences*, vol. 87; pp. 100-111.

Huynh, L.K. "Rational Design of Drug Formulations Using Computational Approaches," Doctoral thesis. Retrieved from https://tspace.library.utoronto.ca/bitstream/1807/35730/8/Huynh_Loan_K_201106_PhD_thesis.pdf. (196 pages.).

* cited by examiner

FRAMEWORK FOR IN-SILICO DESIGN AND TESTING OF VEHICLES AND FORMULATIONS FOR DELIVERY OF ACTIVE MOLECULES

PRIORITY CLAIM

This U.S. patent application claims priority under 35 U.S.C. § 119 to: India Application No. 201921020188, filed on May 21, 2019. The entire contents of the aforementioned application are incorporated herein by reference.

TECHNICAL FIELD

This disclosure relates generally to therapeutic system, and, more particularly, to system and method for in-silico design and testing of vehicles and formulations for delivery of active molecules.

BACKGROUND

In healthcare and personal care industries, a drug delivery system (DDS) is a formulation or a device that enables introduction of a therapeutic substance into the body and improves its efficacy and safety by controlling the rate, time, and place of release of drugs in the body. Some of the common routes of administration include the enteral (gastrointestinal tract), parenteral (via injections), inhalation, transdermal, topical, and oral routes. One of the key challenges in the healthcare and personal care industries is arriving at an optimum delivery vehicle and formulation (for a given active molecule) which can deliver a specified molecule to an intended site of action with minimal or no side effects. The problem becomes more tedious as the active molecule can be delivered through various routes such as intravenous, oral, transdermal, intramuscular to name a few.

A delivery vehicle and a formulation is a key to achieve desired release of the active molecule for a given delivery route of administration and uptake mechanism. For example, controlled release can be achieved by loading drugs/chemicals in a polymer hydrogel. This technology now spans many fields such as pharmaceutical, food and agricultural applications, pesticides, cosmetics, and household products. Currently design of the delivery vehicle and formulation is carried out by trial and error detailed experiments with almost no or vey less digital intervention. To add more complexity, potential formulations are further tested on in-vitro model, animal models (in-vivo). The formulation goes for clinical trials (in Humans) after successful result in the previous stage. In current industry standards, for a drug from its inception to market, it takes eight to ten years and much higher spending and every year several animals are killed for in-vivo testing. Even after that, almost 90 percent of drug are getting failed at various stages of clinical trials.

SUMMARY

Embodiments of the present disclosure present technological improvements as solutions to one or more of the above-mentioned technical problems recognized by the inventors in conventional systems. For example, in one aspect, a processor implemented method of designing and testing of at least one vehicle and formulation for delivery of at least one active molecule is provided. The processor implemented method includes at least one of: receiving, via one or more hardware processors, a plurality of inputs; processing, via the one or more hardware processors, the plurality of inputs to generate a plurality of drug delivery routes; designing, via the one or more hardware processors, at least one vehicle associated with formulation based on a plurality of parameters associated with the active molecule and the plurality of drug delivery routes; testing, via the one or more hardware processors, the designed at least one vehicle associated with the formulation on an in-silico model of a corresponding at least one chosen drug delivery route to obtain a data associated with delivery of the at least one active molecule; and reiteratively processing, via the one or more hardware processors, the data associated with delivery of the at least one active molecule to obtain a desired data associated with the delivery of the at least one active molecule. In an embodiment, the plurality of inputs includes at least one of: (i) an active molecule, (ii) an at least one active molecule chosen by a user from a database, and (iii) a new active molecule from at least one external database.

In an embodiment, the plurality of drug delivery routes may be determined by an action associated with the at least one active molecule. In an embodiment, the at least one active molecule corresponds to a drug molecule. In an embodiment, the action associated with the at least one active molecule may be tuned to a plurality of responses. In an embodiment, the plurality of responses may correspond to at least one of: (i) an instantaneous, (ii) a controlled, (iii) an extended, (iv) a personalized, (v) a pulsatile, and (vi) a desired response for the active molecule. In an embodiment, the plurality of parameters associated with the at least one active molecule and the plurality of drug delivery routes may correspond to at least one of (i) chemical properties of the at least one active molecule, (ii) physical properties of the at least one active molecule, (iii) interaction of the at least one active molecule with the at least one vehicle to be designed, (iv) capacity of the at least one vehicle to be loaded with the at least one active molecule, (v) chemical and physical properties of the at least one vehicle, and (vi) a combination thereof. In an embodiment, the at least one vehicle may correspond to at least one of: a nanomaterial, a supra-biomolecule, a polymer, a hydrogel, a biodegradable material, an organic and inorganic, and combination thereof. In an embodiment, the in-silico model of the plurality of drug delivery routes may be selected from at least one of: (i) a multiscale model, (ii) an empirical relation, (iii) a physics-based model or a data-based model, (iv) a molecular model, (v) a macroscopic model, and combination thereof. In an embodiment, the desired data associated with the delivery of the at least one active molecule may correspond to at least one of: (i) a release profile of the at least active molecule, (ii) a flux of the at least one active molecule, (iii) cumulative amount of the at least one active molecule, (iv) bio-availability of the active molecule, and (v) combination thereof.

In another aspect, there is provided a system to design and test at least one vehicle and formulation for delivery of at least one active molecule. The system comprises a memory storing instructions; one or more communication interfaces; and one or more hardware processors coupled to the memory via the one or more communication interfaces, wherein the one or more hardware processors are configured by the instructions to: receive a plurality of inputs; process, the plurality of inputs to generate a plurality of drug delivery routes; design, at least one vehicle associated with formulation based on a plurality of parameters associated with the active molecule and the plurality of drug delivery routes; test, the designed at least one vehicle associated with the formulation on an in-silico model of a corresponding at least one chosen drug delivery route to obtain a data associated with delivery of the at least one active molecule; and reiteratively process, the data associated with delivery of the at least one active molecule to obtain a desired data associated with the delivery of the at least one active molecule. In an embodiment, the plurality of inputs includes at least one of: (i) an active molecule, (ii) an at least one active molecule chosen by a user from a database, and (iii) a new active molecule from at least one external database.

In an embodiment, the plurality of drug delivery routes may be determined by an action associated with the at least one active molecule. In an embodiment, the at least one active molecule corresponds to a drug molecule. In an embodiment, the action associated with the at least one active molecule may be tuned to a plurality of responses. In an embodiment, the plurality of responses may correspond to at least one of: (i) an instantaneous, (ii) a controlled, (iii) an extended, (iv) a personalized, (v) a pulsatile, and (vi) a desired response for the active molecule. In an embodiment, the plurality of parameters associated with the at least one active molecule and the plurality of drug delivery routes may correspond to at least one of (i) chemical properties of the at least one active molecule, (ii) physical properties of the at least one active molecule, (iii) interaction of the at least one active molecule with the at least one vehicle to be designed, (iv) capacity of the at least one vehicle to be loaded with the at least one active molecule, (v) chemical and physical properties of the at least one vehicle, and (vi) a combination thereof. In an embodiment, the at least one vehicle may correspond to at least one of: a nanomaterial, a supra-biomolecule, a polymer, a hydrogel, a biodegradable material, an organic and inorganic, and combination thereof. In an embodiment, the in-silico model of the plurality of drug delivery routes may be selected from at least one of: (i) a multiscale model, (ii) an empirical relation, (iii) a physics-based model or a data-based model, (iv) a molecular model, (v) a macroscopic model, and combination thereof. In an embodiment, the desired data associated with the delivery of the at least one active molecule may correspond to at least one of: (i) a release profile of the at least active molecule, (ii) a flux of the at least one active molecule, (iii) cumulative amount of the at least one active molecule, (iv) bio-availability of the active molecule, and (v) combination thereof.

In yet another aspect, there are provided one or more non-transitory machine readable information storage mediums comprising one or more instructions which when executed by one or more hardware processors causes at least one of: receiving, a plurality of inputs; processing, the plurality of inputs to generate a plurality of drug delivery routes; designing, at least one vehicle associated with formulation based on a plurality of parameters associated with the active molecule and the plurality of drug delivery routes; testing, the designed at least one vehicle associated with the formulation on an in-silico model of a corresponding at least one chosen drug delivery route to obtain a data associated with delivery of the at least one active molecule; and reiteratively processing, the data associated with delivery of the at least one active molecule to obtain a desired data associated with the delivery of the at least one active molecule. In an embodiment, the plurality of inputs includes at least one of: (i) an active molecule, (ii) an at least one active molecule chosen by a user from a database, and (iii) a new active molecule from at least one external database.

In an embodiment, the plurality of drug delivery routes may be determined by an action associated with the at least one active molecule. In an embodiment, the at least one active molecule corresponds to a drug molecule. In an embodiment, the action associated with the at least one active molecule may be tuned to a plurality of responses. In an embodiment, the plurality of responses may correspond to at least one of: (i) an instantaneous, (ii) a controlled, (iii) an extended, (iv) a personalized, (v) a pulsatile, and (vi) a desired response for the active molecule. In an embodiment, the plurality of parameters associated with the at least one active molecule and the plurality of drug delivery routes may correspond to at least one of (i) chemical properties of the at least one active molecule, (ii) physical properties of the at least one active molecule, (iii) interaction of the at least one active molecule with the at least one vehicle to be designed, (iv) capacity of the at least one vehicle to be loaded with the at least one active molecule, (v) chemical and physical properties of the at least one vehicle, and (vi) a combination thereof. In an embodiment, the at least one vehicle may correspond to at least one of: a nanomaterial, a supra-biomolecule, a polymer, a hydrogel, a biodegradable material, an organic and inorganic, and combination thereof. In an embodiment, the in-silico model of the plurality of drug delivery routes may be selected from at least one of: (i) a multiscale model, (ii) an empirical relation, (iii) a physics-based model or a data-based model, (iv) a molecular model, (v) a macroscopic model, and combination thereof. In an embodiment, the desired data associated with the delivery of the at least one active molecule may correspond to at least one of: (i) a release profile of the at least active molecule, (ii) a flux of the at least one active molecule, (iii) cumulative amount of the at least one active molecule, (iv) bio-availability of the active molecule, and (v) combination thereof.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
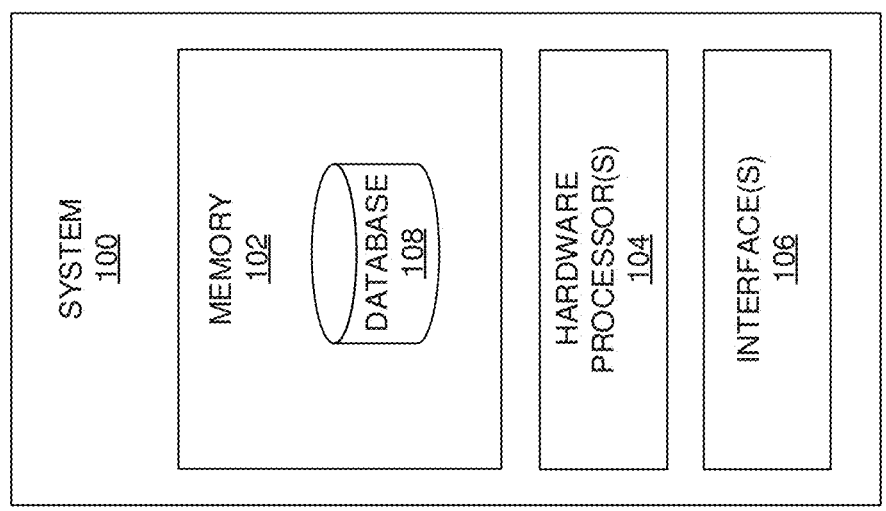
FIG. 1 illustrates a system for in-silico designing and testing of vehicles and formulations for delivery of active molecules, according to embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

Embodiments herein provide a framework and a simulation platform for in-silico design and testing of vehicles and formulations for delivery of active molecules. The embodiments of the present disclosure provide an integrated platform for providing the optimal or best formulations, vehicle design and the route of administration for a given drug molecule and associated release requirements. The proposed formulation design is primed to provide desired release/uptake/bioavailability of active molecule at the site of action to minimize risks associated with complete experimentation-oriented design method prevalent at present. The embodiments of the present disclosure provide an integrated framework to couple multiphysics modeling and simulation techniques or tools to achieve the desired goal.

Referring now to the drawings, and more particularly to FIGS. 1 through 9, where similar reference characters denote corresponding features consistently throughout the figures, there are shown preferred embodiments and these embodiments are described in the context of the following exemplary system and/or method.

FIG. 1 illustrates a system 100 for an in-silico design and testing of vehicles and formulations for delivery of active molecules, according to embodiments of the present disclosure. In an embodiment, the system 100 includes one or more processors 104, communication interface device(s) or input/output (I/O) interface(s) 106, and one or more data storage devices or memory 102 operatively coupled to the one or more processors 104. The memory 102 comprises a database 108. The one or more processors 104 that are hardware processors can be implemented as one or more microprocessors, microcomputers, microcontrollers, digital signal processors, central processing units, state machines, logic circuitries, and/or any devices that manipulate signals based on operational instructions. Among other capabilities, the processor(s) is configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud and the like.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, the memory 102 includes a plurality of modules and a repository for storing data processed, received, and generated by the plurality of modules. The plurality of modules may include routines, programs, objects, components, data structures, and so on, which perform particular tasks or implement particular abstract data types.

The database 108 may store information but are not limited to, information associated with at least one of: (i) data based models, (ii) physics based models, and (iii) plurality of molecules obtained from one or more module e.g., organic molecules, in-organic molecules, and biomolecules. Further, the database 108 stores information pertaining to inputs fed to the system 100 and/or outputs generated by the system 100 (e.g., data/output generated at each stage of the data processing), specific to the methodology described herein. More specifically, the database 108 stores information being processed at each step of the proposed methodology. In an embodiment, the database 108 include a knowledge database.

The repository, amongst other things, includes a system database and other data. The other data may include data generated as a result of the execution of one or more modules in the plurality of modules.

Figure 2:
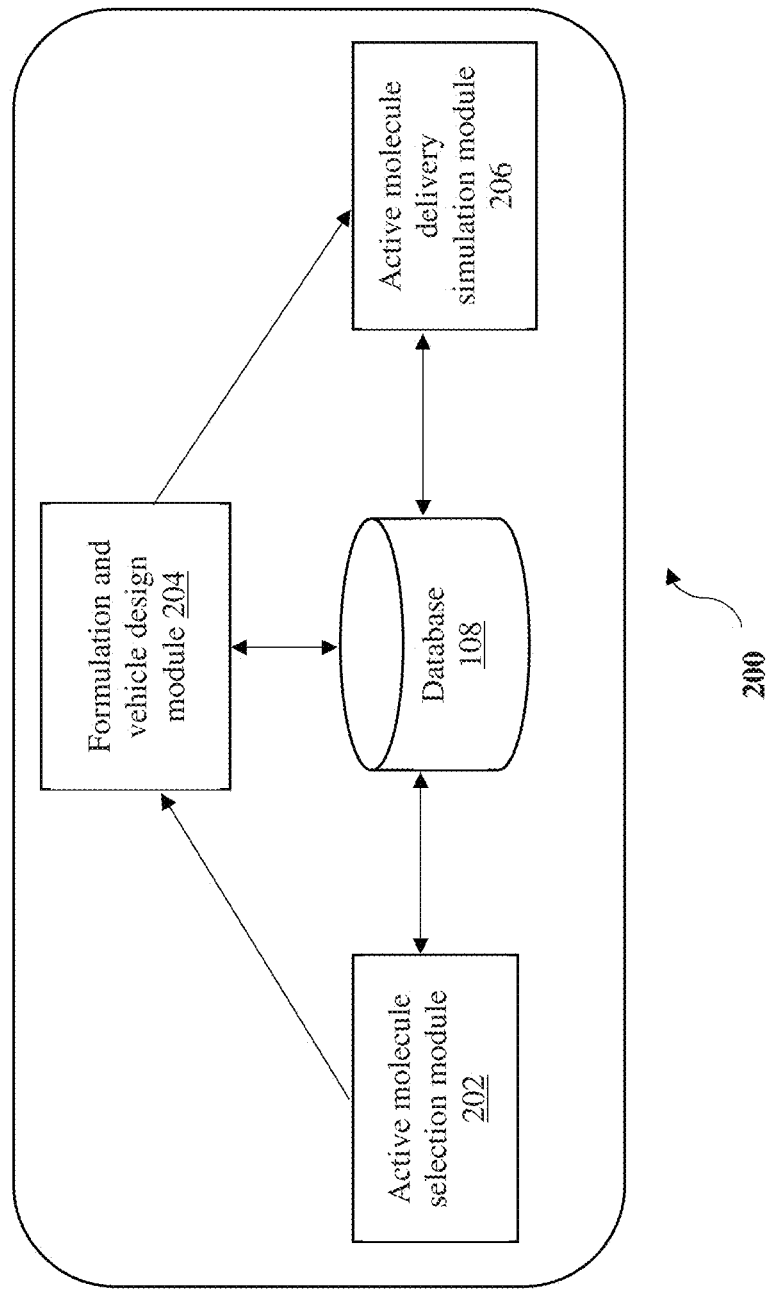
FIG. 2 illustrates an exemplary active molecule delivery system for in-silico design and testing of vehicles and formulations for delivery of active molecules, according to embodiments of the present disclosure.

FIG. 2 illustrates an exemplary active molecule delivery system 200 for the in-silico design and testing of the vehicles and the formulations for the delivery of the active molecules, according to embodiments of the present disclosure. The exploded view of the active molecule delivery system 200 includes an active molecule selection module 202, a formulation and vehicle design module 204, and an active molecule delivery simulation module 206. In an embodiment, the active molecule delivery system 200 is an example implementation of the system 100 of FIG. 1. In an embodiment, but limited to, the active molecule corresponds to a therapeutic molecule, a cosmetic molecule, and a nanoparticle. In another embodiment, the therapeutic molecule may correspond to a drug molecule.

The active molecule selection module 202 is configured to narrow down on preferred route of delivery provided an active molecule and a kinetics of action of the active molecule that can be one of the prescribed forms such as controlled, extended, pulsatile etc. The active molecule selection module 202 is configured to choose an active molecule e.g., a drug candidate, and a user can choose any drug molecule from an available drug database/library or can provide a new drug molecule from a external database. In an embodiment, the user may correspond to but not limited to a therapist, a doctor, and a patient. In an embodiment, the user selects the drug molecule and an associated desired response to move to next sub-module. A one or more delivery routes are chosen based on the drug molecule and response. In an embodiment, plurality of combinations of drug, response and delivery route are generated based on the user's selection.

The formulation and vehicle design module 204 is configured to design a vehicle and formulation and combination of both for different feasible routes of delivery for the given active molecule. In an embodiment, modeling and simulation techniques are applied, given that the material properties to arrive at transport and structural properties of delivery system includes the formulation and the vehicle. In an embodiment, a plurality of vehicle options is chosen by the formulation and vehicle design module 204 based on one or more drug formulations. In an embodiment, the design and the optimization loop are run till a stable and compatible vehicle and formulation combination/s are achieved. In an embodiment, an optimization loop takes/provide an information from/to the knowledge database respectively at every instance. In an embodiment, plurality of structural properties associated with the vehicle and the formulation are either can be feed from an inbuilt information library or can be given input by the user if available or can be dynamically calculated. For example, a drug diffusion through a polymer hydrogel can be calculated using either a molecular dynamics simulation or by an empirical relation which are part of the knowledge database.

In an embodiment, the vehicle and formulation compatibility are checked with one or more modelling and simulation techniques. For example, the one or more modelling and simulation techniques correspond to a molecular simulation, a population balance modelling, a physics-based model, a data-based models, a structure property relationship e.g., a Quantity Structure Property Relationship (QSPR) modeling or retrieving existing information from the knowledge database, and a multiscale modelling. For example, a stability of a nanoparticle formulation is checked by the molecular simulation. In an embodiment, a miscibility of drug and polymer are also checked with a Hansen solubility criterion which is part of the knowledge database.

The active molecule delivery simulation module 206 is configured to perform simulation on in-silico model of the delivery route and targeting organ and/or tissue for the given delivery system and estimates release, bioavailability, uptake, toxicity of the active molecule. The active molecule delivery simulation module 206 is configured to test a designed optimized stable, a compatible vehicle, formulation, and combination of both formulations on the in-silico model of corresponding delivery route chosen by the active molecule selection module 202. In an embodiment, the at least one of formulation, the vehicle, and combination thereof are screened based on the release through the in-silico model, uptake in the in-silico model, bioavailability inside the in-silico model and toxicity. The desired conditions are matched further in-vivo/in-vitro test can be carried out by the user separately. An in-silico model library is active based on the plurality of routes chosen in the active molecule selection module 202. In an embodiment, the drug is chosen to deliver through the plurality of routes. In an embodiment, the user chooses the same in the active molecule selection module 202 and corresponding options are available in the active molecule delivery simulation module 206.

In an embodiment, the in-silico model of routes/a organ are at least from an electronic scale to a macro scale, empirical relations, physics based or databased model. For example, the in-silico model associated with skin includes a molecular model where each constituents of skin's layer are accounted explicitly. The same skin can also a simple multilayer diffusion model where molecular details are not needed/omitted. The user utilizes the knowledge database to select an appropriate model based on one or more applications. For example, to design a skin permeation enhancer, which changes the skin structure at nanoscale, skin's molecular model is needed.

The active molecule delivery simulation module 206 includes one or more models ranging from one or more atomic scales to one or more macro scales such as a molecular model, a CFD models, a FEM models, and a multiscale model. In an embodiment, the active molecule delivery simulation module 206 also include a model based on data and physics and combined with an artificial intelligence (AI) and a machine learning (ML) expertise. In an embodiment, one or more parameters for models can either be provided as an input by the user or obtained from the knowledge database using an empirical relation or one or more simulations. Based on the model, the parameters may be a structural, a transport or a thermodynamics properties of organ, route, formulations, or a drug molecule. In an embodiment, the knowledge database contains a model feasibility information and are updated at every instance if the integrated platform is executed.

Figure 3A:
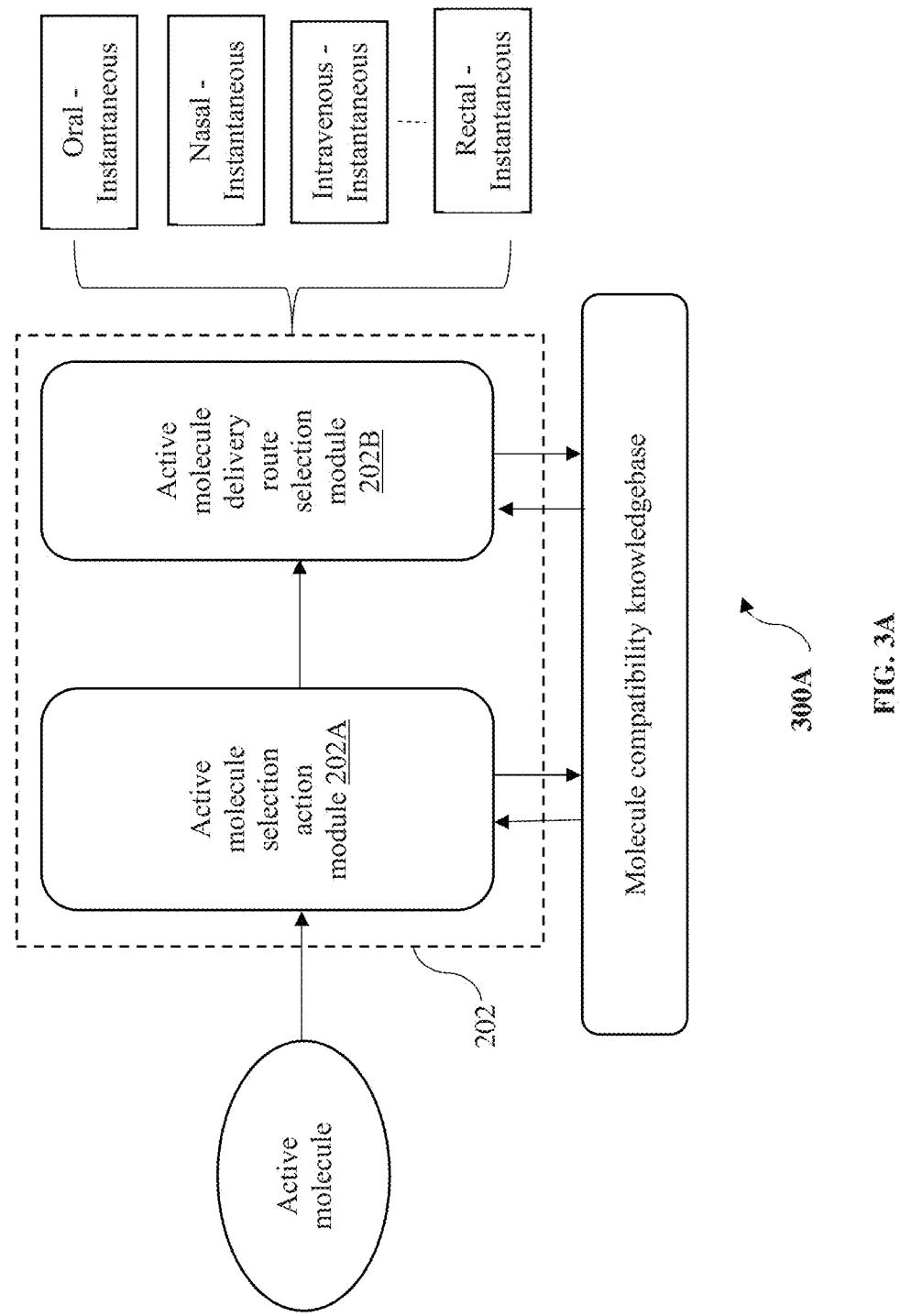
FIG. 3A is an exploded view of an active molecule selection module of the active molecule delivery system, according to embodiments of the present disclosure.

FIG. 3A is an exploded view 300A of the active molecule selection module 202 of the active molecule delivery system 200, according to embodiments of the present disclosure. The active molecule selection module 202 is configured to choose an active molecule candidate. In an embodiment, a user can select at least one active molecule from available active molecule database/library or can provide a new active molecule from an external database. The active molecule selection module 202 further includes an active molecule action module 202A which includes an information related to desired release of the molecule i.e. a flux, a rate, an amount, bioavailability etc. In an embodiment, action of the active molecule can be tuned to plurality of responses but not limited to such as instantaneous, controlled, extended, personalized, pulsatile etc. The user further selects desired response from the plurality of responses for the molecule to move to next sub-module. In an embodiment, one or more delivery routes can be feasible based on active molecule and desired response.

The active molecule selection module 202 further includes an active molecule delivery route selection module 202B that is configured to select a delivery route. In an embodiment, the one or more delivery routes are but not limited to at least one of: (a) oral, intravenous, subcutaneous, intramuscular, nasal, transdermal, rectal, and topical. A plurality of plausible combinations of desired response and delivery routes for the given active molecule are generated. The combinations can be further screened based on information provided to the user from the active molecule-response-route compatibility database. For example, delivery of drug molecule (drug can be such intended active molecule) through topical route is mostly not instantaneous while oral delivery lack in providing sustained/extended release. In an embodiment, an active molecule compatibility knowledge base is updated at every instance of platform being used. The information from each sub-module goes and back and forth at any time and can be tracked.

Figure 3B:
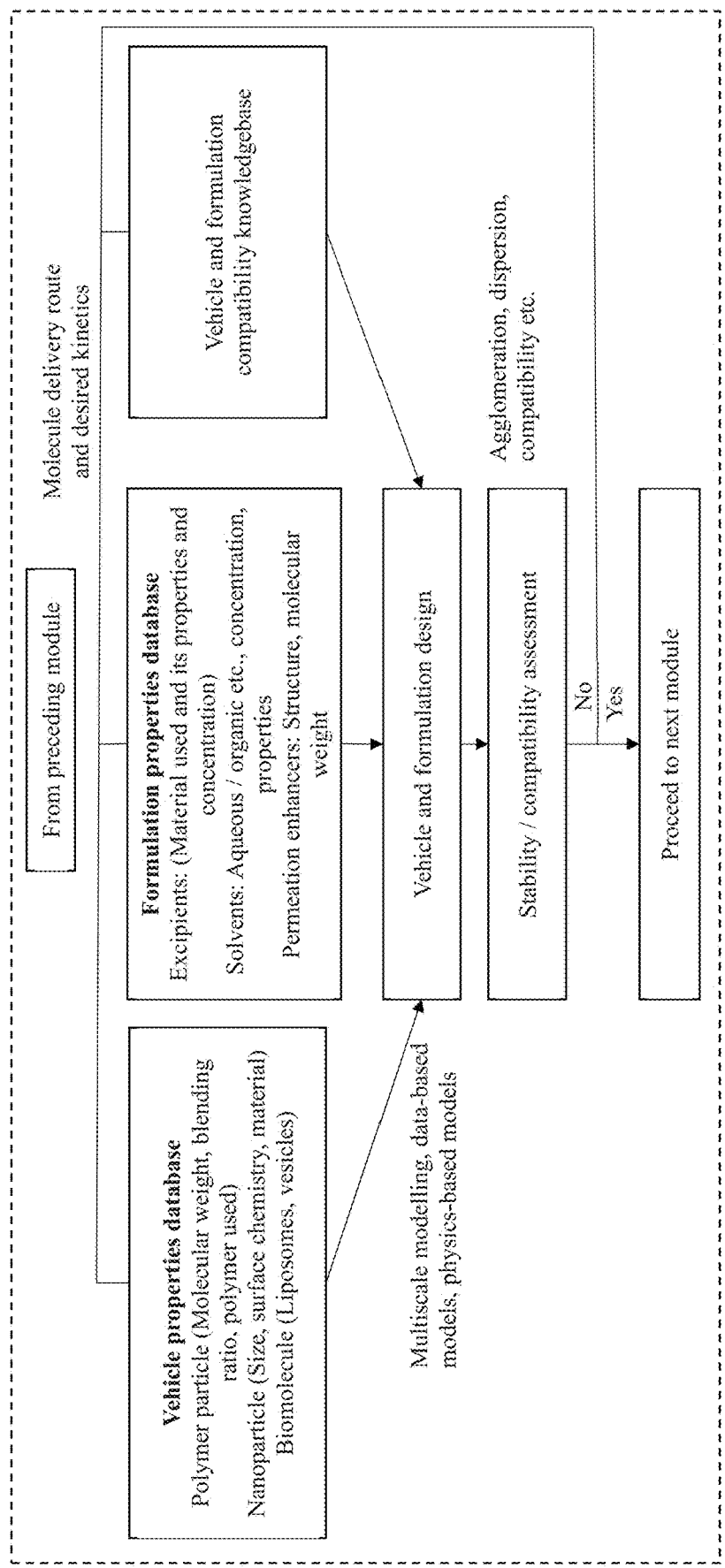
FIG. 3B is a block diagram of a formulation and vehicle design module of the active molecule delivery system for design and testing of vehicles and formulations, according to embodiments of the present disclosure.

FIG. 3B is a block diagram of the formulation and vehicle design module 204 of the active molecule delivery system 200 for design and testing of vehicles and formulations, according to embodiments of the present disclosure. The formulation and vehicle design module 204 is configured to design vehicle and formulation and combination of both for different feasible delivery routes narrowed in the active molecule selection module 202. In an embodiment, the design and optimization loop is run till stable and compatible vehicle and formulation combination/s are achieved. In an embodiment, the optimization loop changes or adapts the material properties of vehicle and formulation while also assessing the feasibility of the synthesis of the vehicle and formulation experimentally. The optimization loop takes/gives information from/to the knowledge database at periodic intervals pertaining to the optimized vehicle and formulation for a given active molecule, delivery route and intended action.

In an embodiment, plurality of properties associated with vehicle and formulation is enabled for vehicle and formulation design which can be estimated/populated. The vehicle and formulation design which can be estimated/populated by at least one of (i) populating the plurality of properties from the inbuilt information library based on the material's used to synthesize vehicle and formulation, (ii) being defined by the user in the platform, (c) can also be calculated using defined expressions/equations, and combination thereof. For example, polymer molecular weight used to synthesize polymer based vehicles can be defined by user or can be calculated in the platform based on monomer/s and the number of monomers used to synthesize polymer or can be estimated platform given spectra from gel permeation chromatography.

In an embodiment, the vehicle properties are dependent on type of material used, so for a polymer particle and can include but not limited to at least one of associated molecular weight, monomers used, size of particle. In an embodiment, the formulation parameters include at least one of concentrations of excipients, solvents, and permeation enhancers used. In an embodiment, given the properties of vehicle and formulation, the vehicle formulation and design module estimates transport and structural properties of the package (the vehicle and formulation) using at least one of different modeling and simulation techniques such as molecular simulations, a computational fluid dynamics, a population balance modeling, finite-element method.

In an embodiment, the vehicle may be part of formulation or formulation can be loaded/embedded inside or in the interior of the vehicle. In an embodiment, a phase of the vehicle may be but not limited to in a liquid, a solid, a gel and a multiphase system or a combination thereof. In an embodiment, the vehicle may also be in form of liquid, solid, gel and multiphase system or combination thereof. In an embodiment, the vehicle may be a nanomaterials, a suprabiomolecules (e.g., Liposomes, vesicles), a polymer, hydrogels, and biodegradable materials, organic and inorganic, or combination thereof. In an embodiment, the vehicle may be of any shape (e.g., cylindrical, disc etc.), form (e.g., tablets, capsules etc.), phase (e.g., solid, liquid, gel etc.), size. In an embodiment, the formulation may be any form and phase, solid, liquid, aerosol, foam, multiphase system. The listed forms of formulation are for illustration purpose and should not be treated as a set of exhaustive options. In an embodiment, the formulation can include nanomaterials, biomaterials, chemicals, organic and inorganic molecules, aqueous and organic solvents, pH modifiers, viscosity modifiers etc.

Figure 3C:
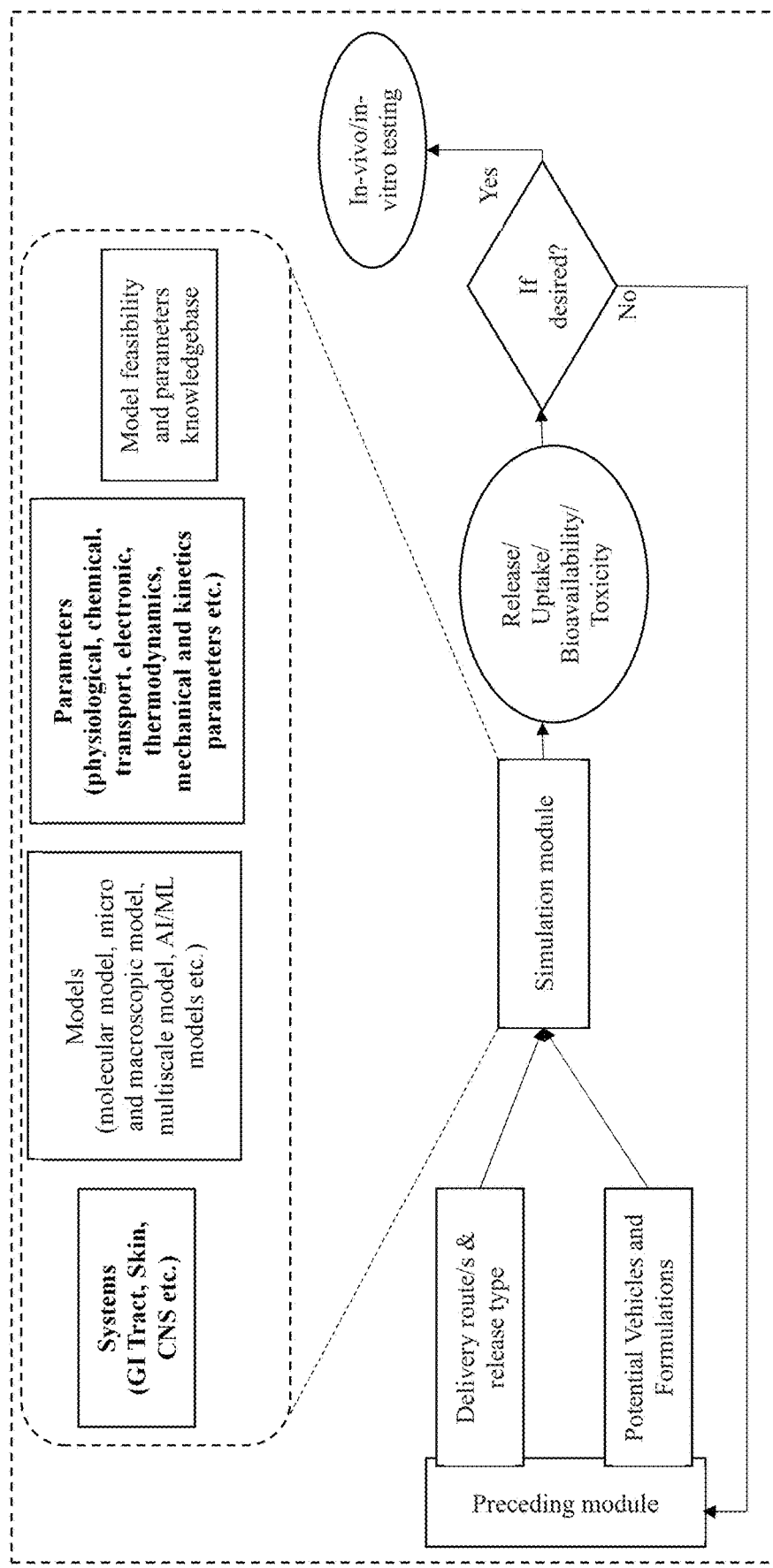
FIG. 3C is a block diagram of an active molecule delivery simulation module of the active molecule delivery system for in-silico testing of vehicles and formulations, according to embodiments of the present disclosure.

FIG. 3C is a block diagram of the active molecule delivery simulation module 206 of the active molecule delivery system 200 for in-silico testing of vehicles and formulations, according to embodiments of the present disclosure. In an embodiment, the designed, optimized stable and compatible vehicle, formulation or combination of both are tested on the in-silico models of corresponding delivery route chosen in the active molecule selection module 202. Based on the release simulations, uptake, bioavailability, toxicity and other such release parameters of interest are estimated and the formulation/vehicle/combination of both are screened. Once the desired conditions are matched further in-vivo/in-vitro tests can be carried out by user separately on the prescribed delivery vehicle and formulation. In an embodiment, the in-silico models in the library are activated based on the delivery routes identified as compatible for the given active molecule in the active molecule selection module 202. An active molecule can be compatible for delivery through various routes to achieve the desired release/action/uptake at the site of action.

In an embodiment, the in-silico model associated with one or more routes or organs or tissues, depending on the availability, can vary from electronic scale to macro scale, empirical, physics based or data-based. For example, the in-silico model of skin can be a molecular model where each constituent of skin's layer is accounted for explicitly. The same skin can also be represented a simple multilayer diffusion model where molecular details are not needed/omitted. In an embodiment, the user requests the knowledge database to select the appropriate model based on the application. For example, to design a skin permeation enhancer, which changes the skin structure at nanoscale, skin's molecular model is needed.

In an embodiment, the model parameters can be either provided as an input by user or can be obtained from the knowledge database or using empirical relation. Based on the model, the parameters can be structural, transport or thermodynamics properties of organ, route, formulations or active molecule to be delivered. In an embodiment, the knowledge database includes model feasibility information which, based on the selected delivery vehicle, formulation or the combination of both along with the type of in-silico model of the delivery route decides whether it is computationally feasible to carry out in-silico simulation in stipulated amount of time. The knowledge database in updated at every instance of platform is executed.

Figure 4A:
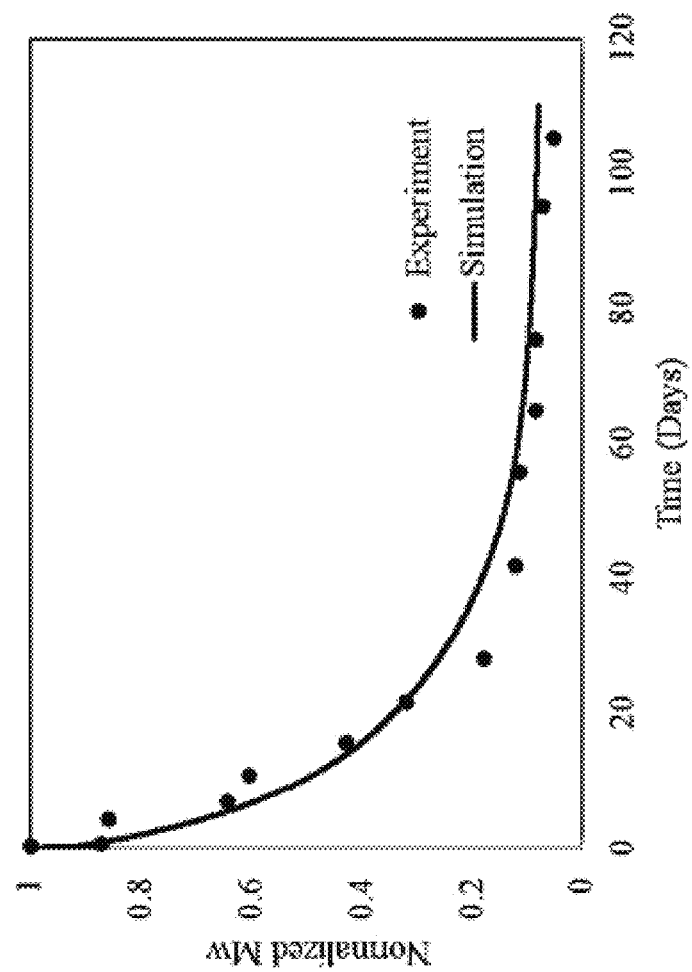
FIG. 4A is an exemplary graphical representation illustrating a prediction of change in a molecular weight of a poly-lactic-co-glycolic acid (PLGA) in a microparticle in the active molecule delivery system, according to embodiments of the present disclosure.
Figure 4B:
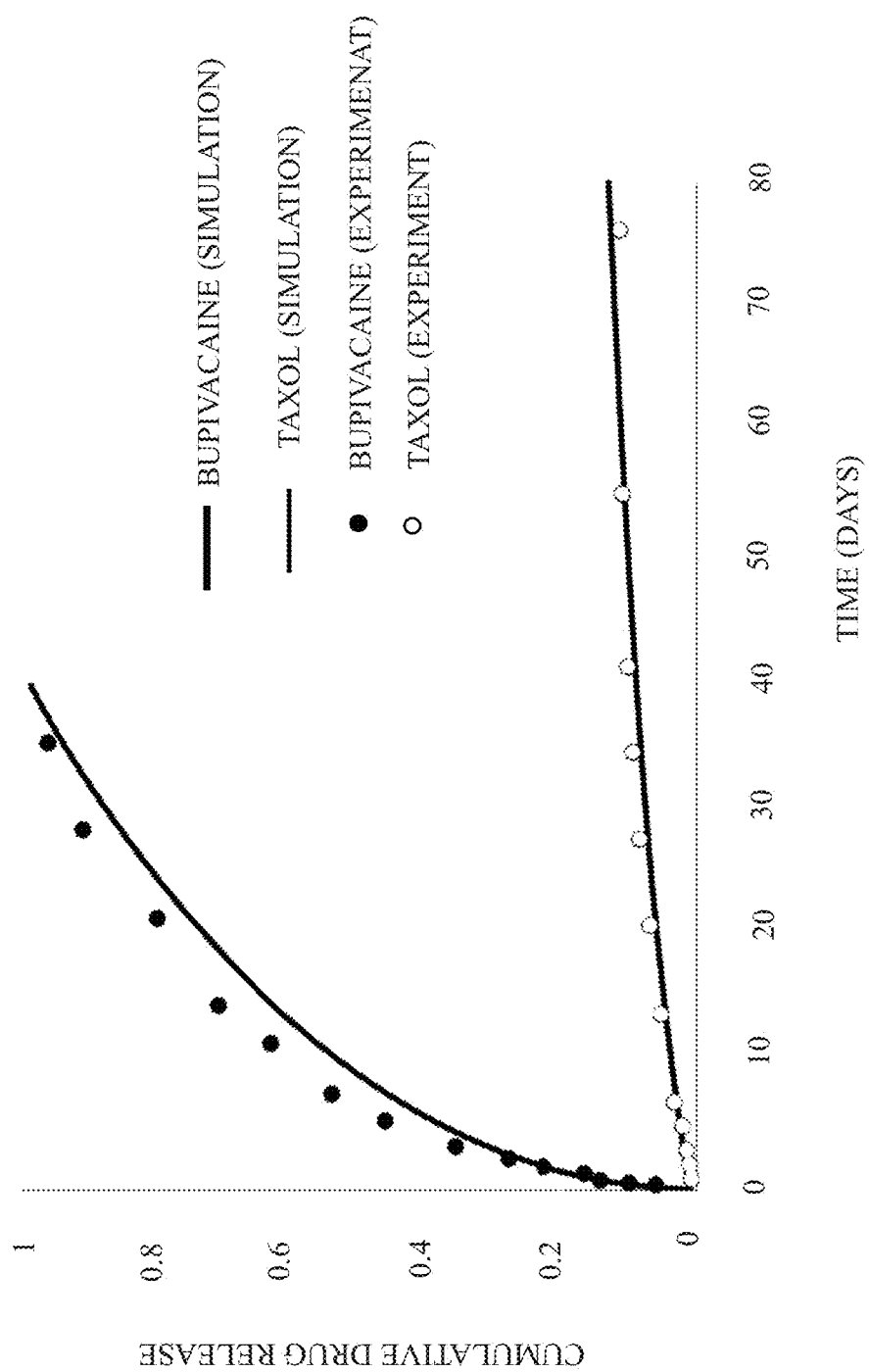
FIG. 4B is an exemplary graphical representation illustrating a prediction of a drug release from a polyanhydride polymer through the active molecule delivery system, according to embodiments of the present disclosure.

FIG. 4A is an exemplary graphical representation illustrating a prediction of change in a molecular weight of PLGA in a microparticle due to a hydrolytic degradation in the active molecule delivery system 200, according to embodiments of the present disclosure. FIG. 4B is an exemplary graphical representation illustrating a prediction of a drug release from a polyanhydride polymer through the active molecule delivery system 200, according to embodiments of the present disclosure. In an exemplary embodiment, a physics-based models that can be used in the formulation and vehicle design module 204. For example, a model to estimate transport and structural properties of microparticles/nanoparticles derived from a polyesters (e.g., polymer with ester groups such as polylactic acid (PLA), poly(lactic-co-glycolic acid) (PLGA)):

$$\frac{dR_{am}}{dt} = k_1^{am} C_e^{am} C_w + k_2^{am} C_e^{am} C_w C_{COOH}^{am\ 1/2}$$

$$\frac{dR_{crys}}{dt} = k_1^{crys} C_e^{crys} C_w + k_2^{crys} C_e^{crys} C_w C_{COOH}^{crys\ 1/2}$$

$$\frac{R_{ol}}{C_{e0}} = \alpha \left(\frac{R_s}{C_{e0}}\right)^\beta$$

$$C_{COOH} = \frac{C_{ol}}{m}$$

$$N_{dp} = \frac{C_{e0} - R_{ol} - \omega_0(X_c - X_{c0})}{N_{chain}}$$

$$\frac{\partial C_{ol}}{\partial t} = \dot{R}_{ol} - D_{ol} \frac{\partial^2 C_{ol}}{\partial x^2}$$

$$\frac{\partial N_{chain}}{\partial t} = \dot{R}_s - D_{N_{chain}} \frac{\partial^2 N_{chin}}{\partial x^2}$$

$$\frac{dX_c}{dX_{ext}} = (1 - X_c)^\lambda$$

$$X_{ext} = pv_c R_{am}$$

$$\frac{\partial C_w}{\partial t} + \nabla \cdot (-D_w \nabla C_w) = -(\dot{R}_{am} + \dot{R}_{crys})$$

$$\frac{\partial C_{Dr}^S}{\partial t} = -k_{dis} C_w C_{Dr}^S$$

$$\frac{\partial C_{Dr}}{\partial t} + \nabla \cdot (-D_{Dr} \nabla C_{Dr}) = k_{dis} C_w C_{Dr}^S$$

where,
$R_s^{am}$: Random scission concentration in amorphous phase
$R_s^{crys}$: Random scission concentration in crystalline phase
$k_1^{am}$: Reaction rate constant of hydrolysis reaction in amorphous phase
$k_2^{am}$: Reaction rate constant of autocatalytic reaction in amorphous phase
$C_e^{am}$: Concentration of ester bonds in the amorphous phase
$k_1^{crys}$: Reaction rate constant of hydrolysis reaction in crystalline phase
$k_2^{crys}$: Reaction rate constant of autocatalytic reaction in crystalline phase
$C_e^{crys}$: Concentration of ester bonds in the amorphous phase
$C_w$: Concentration of water
$C_{COOH}$: Concentration of carboxylic acid
$R_{ol}$: Oligomer concentration produced
$G_{e0}$: Initial concentration of ester groups in the polymer
$C_{ol}$: Concentration of oligomer in the device
$N_{dp}$: Number degree of polymerization
$N_{chain}$: Number of chains of polymers present
$X_c$: Crystallinity of the device
$X_{ext}$: Extended degree of crystallinity of the device
$\omega_0$: Inverse molar volume of crystalline phase
$D_{ol}$: Diffusion coefficient of oligomer
$D_{N_{chain}}$: Diffusion coefficient of small polymeric chains
$k_{dis}$: Dissolution rate constant of drug
$C_{Dr}^S$: Concentration of drug in solid form $C_{Dr}$: Concentration of dissolved drug The coupled model provides a prediction of the evolution of transport and structural properties such as a molecular weight and a crystallinity of the polymer, a mass of the vehicle, and a release rate of the drug from the vehicle.

Figure 5A:
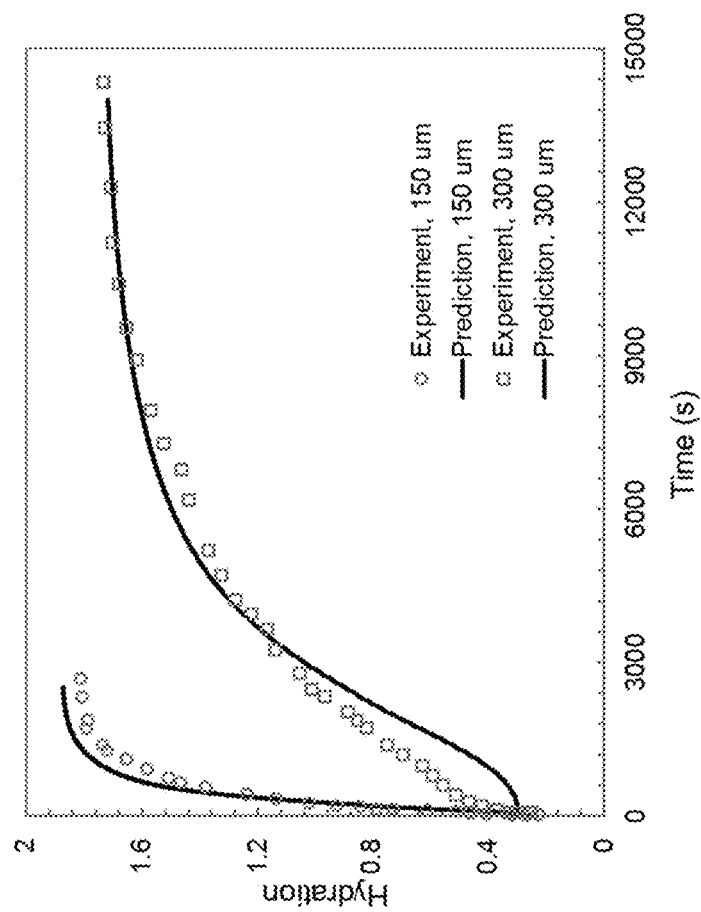
FIG. 5A is an exemplary graphical representation illustrating a prediction of change in size of a pH sensitive hydrogel with time in response to change in surrounding pH, according to embodiments of the present disclosure.
Figure 5B:
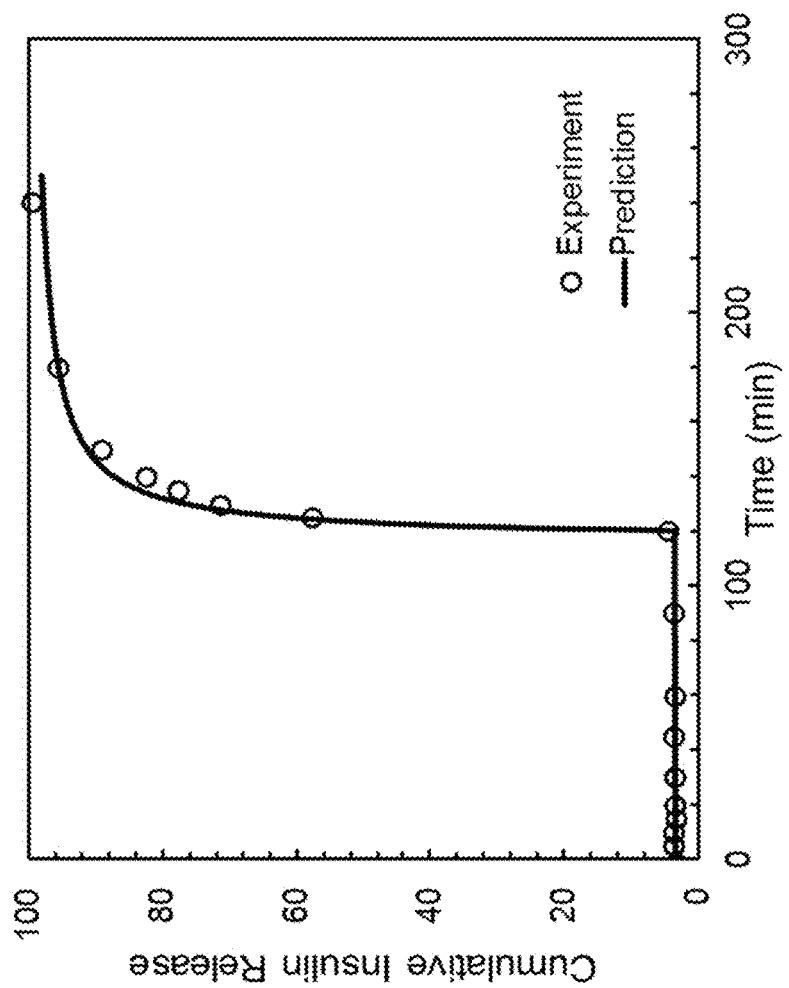
FIG. 5B is an exemplary graphical representation illustrating a prediction of release of an insulin from pH sensitive hydrogel, according to embodiments of the present disclosure.

FIG. 5A is an exemplary graphical representation illustrating a prediction of change in size of a pH sensitive hydrogel with time in response to change in the surrounding pH, according to embodiments of the present disclosure. FIG. 5B is an exemplary graphical representation illustrating a prediction of release of the active molecule (e.g., insulin) from pH sensitive hydrogel, according to embodiments of the present disclosure. For example, the prediction of release of an insulin (active molecule) from pH sensitive hydrogel in response to change in pH from 2 to 7.4. In another exemplary embodiment, a model to estimate transport and structural properties of vehicle based on stimuli sensitive polymer hydrogels (pH):

$$\frac{\partial c_i}{\partial t} + \nabla \cdot (-\overline{D}_i \nabla c_i - z_i \mu_i F c_i \nabla \psi) = 0$$

$$\frac{\overline{D}_i}{D_i} = \left(\frac{H}{2+H}\right)^2$$

$$\frac{\partial c_i}{\partial t} + \nabla \cdot (-D_i \nabla c_i) = 0$$

$$\nabla^2 \psi = -\frac{\rho_v}{\epsilon \epsilon_0}$$

$$\rho_v = F\left(\sum_{i=1}^{3} z_i c_i + z_f c_f\right)$$

$$c_f = \frac{1}{H} \frac{c_{mo}^s K_a}{(K_a + c_H)}$$

$$\rho \frac{\partial^2 u}{\partial t^2} - \nabla S = F_v$$

where,
$c_i$: Concentration of species, $i \in \{Na^+, Cl^-, H^+, Drug\}$
$C_0$=Ionic strength of the surrounding medium, 200 mol/m$^3$
$c_{mo}^s$=Initial concentration of fixed charged groups in hydrogel, 2100 mol/m$^3$
$D_i$: Diffusion of $i^{th}$ species in water, $i \in \{Na^+, Cl^-, H^+, Drug\}$
$\overline{D}_1$: Diffusion coefficient of ith species in gel, $i \in \{Na^+, Cl^-, H^+, Drug\}$
$E_Y$: Elastic modulus of gel, $0.23 \times 10^6$ Pa to $0.29 \times 10^6$ Pa
F: Faraday's constant
H: Hydration state
$K_a$=Dissociation constant of fixed charged carboxylic acid group, $10^{-1.5}$ mol/M$^3$
$P_{osmotic}$: Osmotic pressure
$\psi$: Electric Potential
$\mu_i$: Mobility of the $i^{th}$ ionic species, $i \in \{Na^+, Cl^-, H^+\}$
$\rho_v$: Charge density inside the gel
$\rho_{s0}$: Density of hydrogel at dry state, 1300 kg/m$^3$
$\rho_w$: Density of water, 1000 kg/m$^3$
$\in$: Relative permittivity of water
$\in_0$: Permitivitty of vacuum The coupled model provides a prediction of the evolution of transport and structural properties such as a size of the polymer hydrogel, a charge density of vehicle, and a rate of drug release from the hydrogel.

Figure 6A:
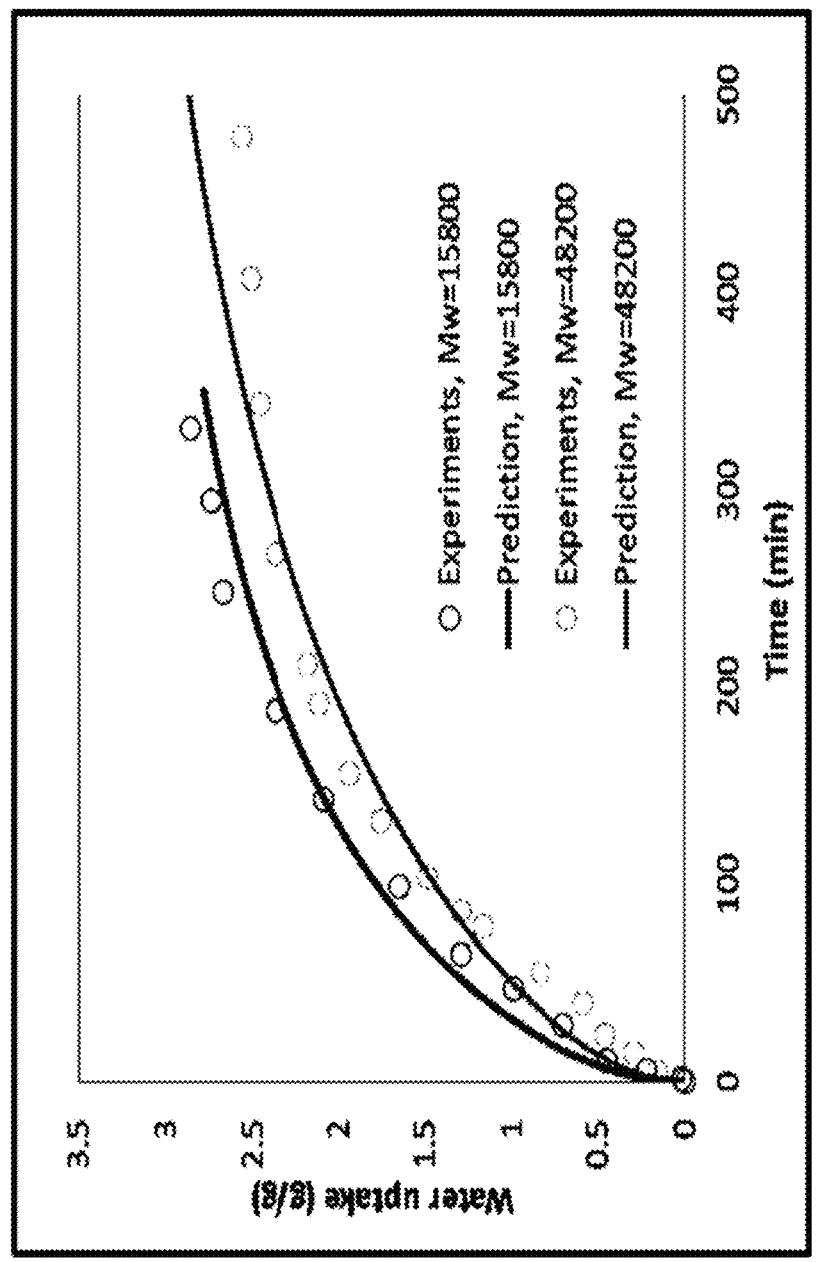
FIG. 6A is an exemplary graphical representation illustrating a prediction of a water uptake by a Poly-vinyl alcohol (PVA) hydrogels with different molecular weights, according to embodiments of the present disclosure.
Figure 6B:
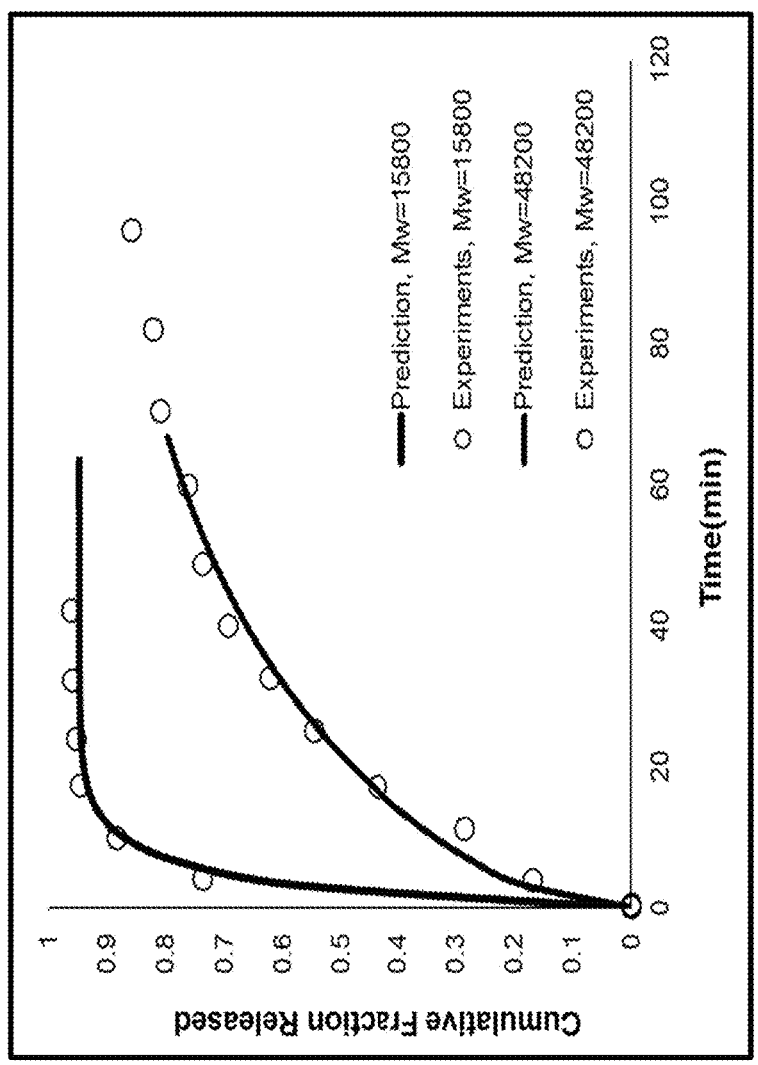
FIG. 6B is an exemplary graphical representation illustrating a prediction of a theophylline release from the Poly-vinyl alcohol (PVA) hydrogels with different molecular weights, according to embodiments of the present disclosure.

FIG. 6A is an exemplary graphical representation illustrating a prediction of a water uptake by a Poly-vinyl alcohol (PVA) hydrogels with different molecular weights, according to embodiments of the present disclosure. FIG. 6B is an exemplary graphical representation illustrating a prediction of the active molecule (e.g., a theophylline) release from the Poly-vinyl alcohol (PVA) hydrogels with different molecular weights, according to embodiments of the present disclosure.

In another exemplary embodiment, a model to estimate transport and structural properties of vehicle based on a hydrophilic polymer hydrogels:

$$\varphi_p^{-5/3} = \frac{v_s M_c}{v_p\left(1 - \frac{2M_c}{M}\right)}\left(\frac{1}{2} - \chi_{sn}\right)$$

$$\xi = \varphi_p^{-\frac{1}{3}}\left(\frac{2C_n M_c}{M_m}\right)l$$

$$\rho\frac{\partial \omega_i}{\partial t} = -(v.\nabla \omega_i) - (\nabla .J_i) + r_i$$

$$J_i = \rho D_i^{gel} \nabla \omega_i$$

$$\frac{\partial \omega_w}{\partial t} = -(\nabla .J_w)$$

$$\rho\frac{\partial \omega_{d_w}}{\partial t} = -(\nabla .J_{d_w}) + r_{diss}$$

$$r_{diss} = k_{diss}\omega_{d_s} w_n$$

$$\frac{\partial (\rho\omega_{d_s})}{\partial t} = -k_{diss}\rho\omega_{d_s} w_n$$

$$\frac{1}{\rho} = \frac{\omega_w}{\rho_w} + \frac{\omega_{d_w}}{\rho_d} + \frac{(1 - \omega_w - \omega_{d_w})}{\rho_p}$$

$$\frac{dS}{dt} = D_w^{gel}\omega_w^{eq}\nabla .\omega_w$$

Where subscript "i" stands for $i^{th}$ species in hydrogel. (for water i=w, and solvent=s)
$D_i^{gel}$, is the diffusion coefficient of species i in the hydrogel.
$\omega_i$ mass fraction of the $i^{th}$ species in hydrogel (i=water (w), drug ($d_w$) and polymer (p))
$k_{diss}$ is dissolution rate constant,
$\omega_{d_s}$ is the concentration of solid drug in the hydrogel $$\left(\frac{kg}{m^3}\right)$$

$w_n$ is the normalized weight fraction of water.
ρ density of hydrogel
S hydrogel swelling rate The coupled model provides prediction of the evolution of transport and structural properties such as an uptake of water by the polymer hydrogel, and a rate of drug release from the hydrogel.

Figure 7A:
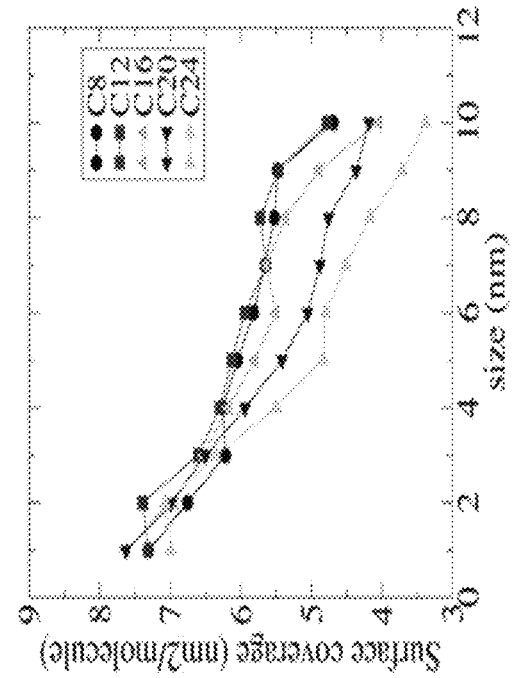
FIGS. 7A-7C is an exemplary graphical representations illustrating a result upon considering a nanoparticle as an at least one vehicle for delivery of the at least one active molecule, according to embodiments of the present disclosure.
Figure 7B:
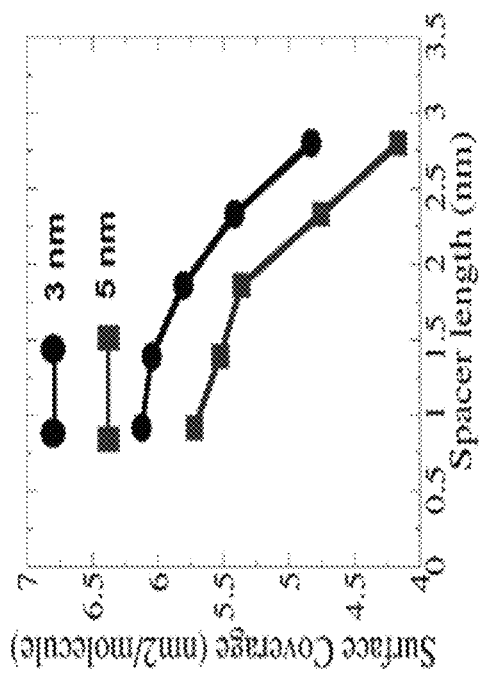
Figure 7C:
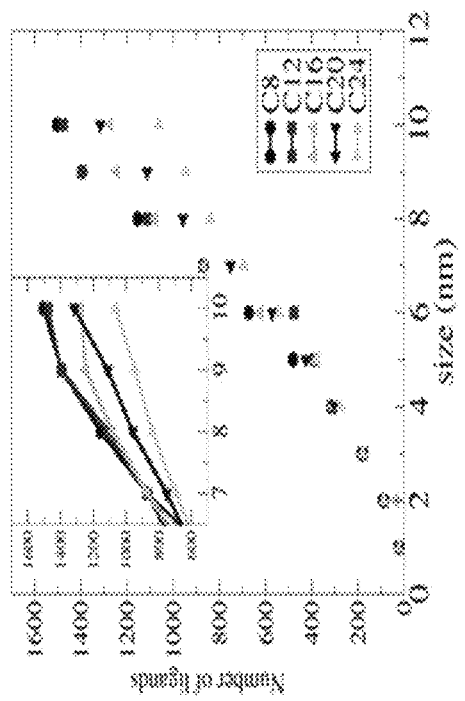

FIGS. 7A-7C is an exemplary graphical representations illustrating a results upon considering a nanoparticle as an at least one vehicle for delivery of the at least one active molecule, according to embodiments of the present disclosure. In an exemplary embodiment, the nanoparticle is considered as a delivery vehicle with a sphere-shaped nanoparticle and the nanoparticle may be made up of at least one of a polymer, a metallic or a bio molecules to determine a surface chemistry and properties. For example, the metallic nanoparticle is utilized due to hydrophobic in nature. A surfactant molecules is identified which needs to be put together when nanoparticles are formed in order to reduce an agglomeration of the nanoparticles. For example, a thiol-based ligands (the surfactant molecules) is used which is having various chain length and identified their maximum coverage on the nanoparticle. Upon identification of a maximum number of ligands that can be coated on the surface of the nanoparticle, next task is to make sure that these nanoparticles should not agglomerate once put together in the formulations by performing the molecular dynamics simulations. For example, the multiple nanoparticles are kept in appropriate conditions like temperature, pressure, concentration, pH etc.

The data used in the design of the nanoparticle system based on the one or more molecular dynamics simulation is as listed in below Table. 1:

TABLE 1

| Nanoparticle Type | Coverage | Results Nanoparticles = 4 | Nanoparticles = 8 |
|---|---|---|---|
| Anionic | 20 | Aggregates | Aggregates |
|  | 40 | Aggregates | Aggregates |
|  | 60 | Small aggregates | Small aggregates |
|  | 80 | Dispersed | Dispersed |
|  | 100 | Dispersed | Dispersed |
| Neutral | 20 | Aggregates | Aggregates |
|  | 40 | Aggregates | Aggregates |
|  | 60 | Aggregates | Aggregates |
|  | 80 | Aggregates | Aggregates |
|  | 100 | Dispersed | Dispersed |
| Cationic | 20 | Aggregates | Aggregates |
|  | 40 | Aggregates | Aggregates |
|  | 60 | Small aggregates | Small aggregates |
|  | 80 | Dispersed | Dispersed |
|  | 100 | Dispersed | Dispersed |

Figure 8A:
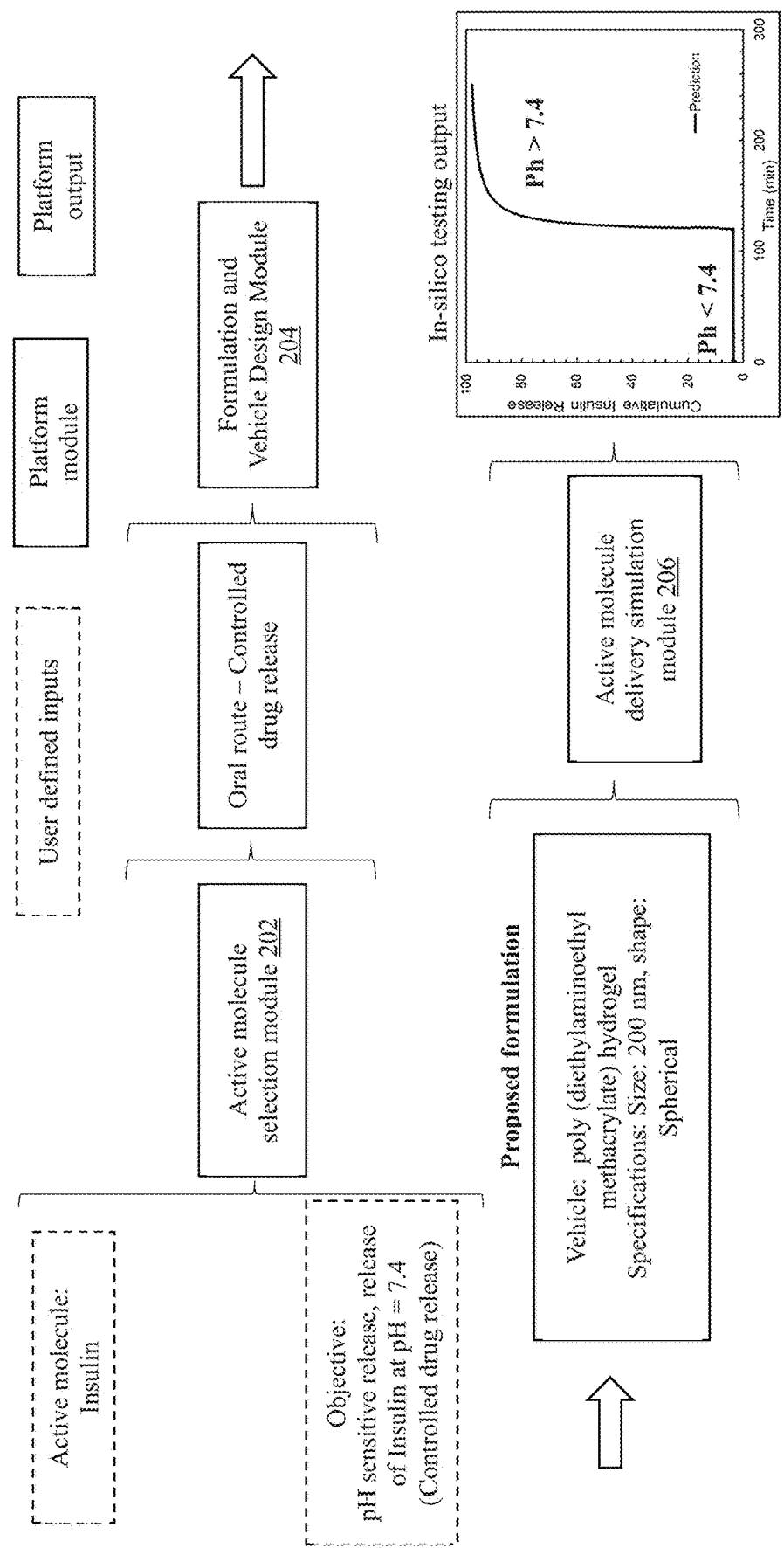
FIG. 8A is an exemplary view illustrating the design and testing of the vehicles and the formulations for delivery of the active molecule through an oral delivery route, according to embodiments of the present disclosure.

FIG. 8A is an exemplary view illustrating the design and testing of the vehicles and the formulations for delivery of the active molecule through an oral delivery route, according to embodiments of the present disclosure. In an exemplary scenario, an objective of designing a formulation for pH sensitive insulin delivery is considered. The active molecule selection module 202 narrows down on the oral route for pH-controlled release of the insulin. The formulation and vehicle design module 204, designs and prescribes poly (diethylaminoethyl methacrylate) hydrogel with the following specifications: Size: 200 nm, shape: spherical, to be used for pH sensitive insulin delivery. The active molecule delivery simulation module 206 simulates and predicts the release of Insulin using the in-silico model of Gastrointestinal (GI) tract.

Figure 8B:
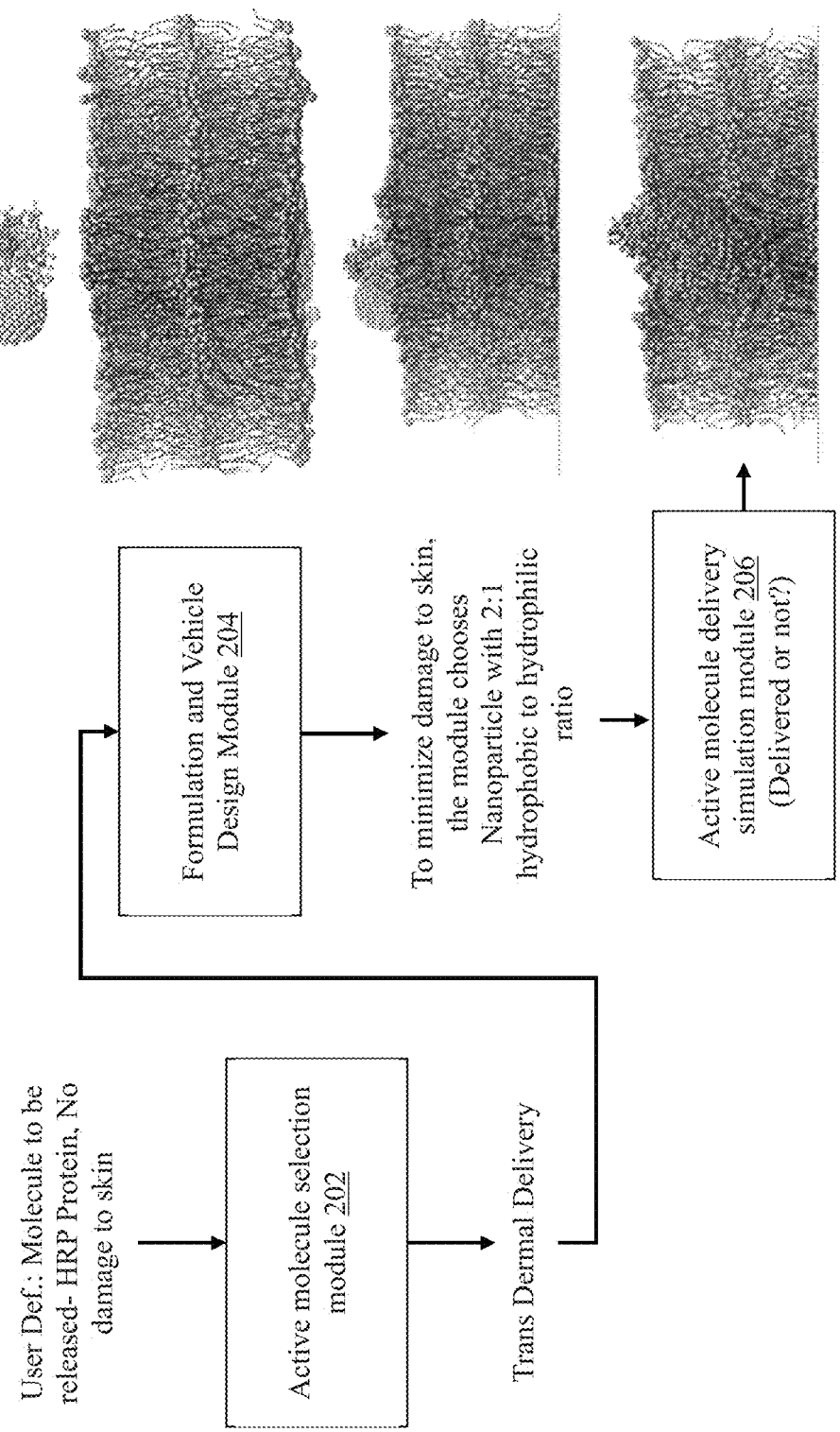
FIG. 8B is an exemplary view illustrating the design and testing of the vehicles and the formulations for delivery of the active molecule through a transdermal delivery route, according to embodiments of the present disclosure.

FIG. 8B is an exemplary view illustrating the design and testing of the vehicles and the formulations for delivery of the active molecule through a transdermal delivery route, according to embodiments of the present disclosure. In an exemplary scenario, consider a HRP (Horseradish peroxidase) protein as the active molecule to be released such that there is no damage to skin. The HRP proteins have an issue of bioavailability when taken orally as compared to transdermal delivery. Based on this knowledge obtained from knowledge base the active molecule selection module 202 choses transdermal delivery as a route of delivering the HRP protein. The formulation and vehicle design module 204 designs nanoparticle with 2:1 hydrophobic to hydrophilic ratio to minimize damage to skin. The active molecule delivery simulation module 206 further validates whether the HRP protein is delivered to destination point of the subject.

Figure 9:
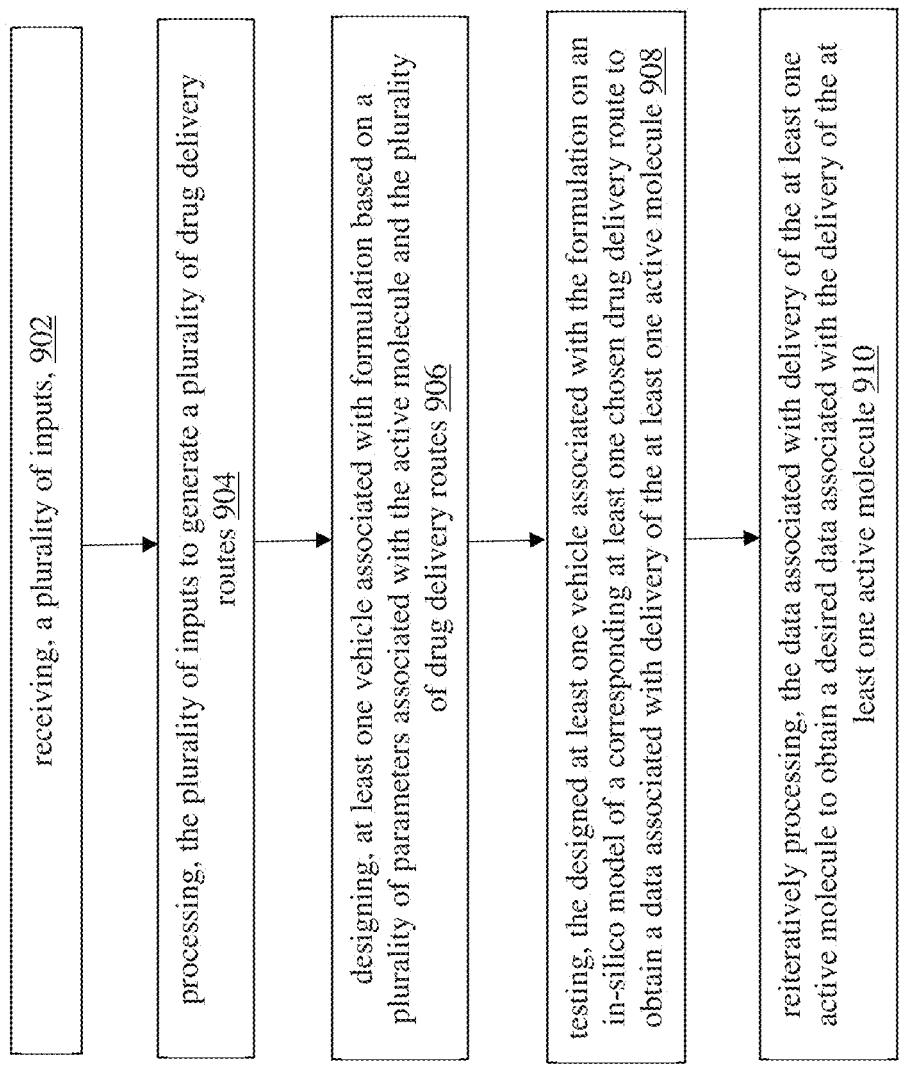
FIG. 9 is an exemplary flow diagram illustrating a method of designing and testing of the at least one vehicle and the formulation for delivery of the at least one active molecule, according to embodiments of the present disclosure.

FIG. 9 is an exemplary flow diagram illustrating a method of designing and testing of the at least one vehicle and the formulation for delivery of the at least one active molecule, according to embodiments of the present disclosure. In an embodiment, the system 100 comprises one or more data storage devices or the memory 102 operatively coupled to the one or more hardware processors 104 and is configured to store instructions for execution of steps of the method by the one or more processors 104. The flow diagram depicted is better understood by way of following explanation/description. The steps of the method of the present disclosure will now be explained with reference to the components of the system as depicted in FIGS. 1 and 2.

At step 902, a plurality of inputs is received. In an embodiment, the plurality of inputs includes at least one of: (i) a chosen active molecule, (ii) an at least one active molecule chosen by a user from a database, and (iii) a new active molecule from at least one external database. At step 904, the plurality of inputs is processed to generate a plurality of drug delivery routes. In an embodiment, the plurality of drug delivery routes may be determined by an action associated with the at least one active molecule. In an embodiment, the at least one active molecule corresponds to a drug molecule. In an embodiment, the action associated with the at least one active molecule may be tuned to a plurality of responses. In an embodiment, the plurality of responses may correspond to at least one of: (i) an instantaneous, (ii) a controlled, (iii) an extended, (iv) a personalized, (v) a pulsatile, and (vi) a desired response for the active molecule.

At step 906, at least one vehicle associated with formulation is designed based on a plurality of parameters associated with the active molecule and the plurality of drug delivery routes. In an embodiment, the plurality of parameters associated with the at least one active molecule and the plurality of drug delivery routes may correspond to at least one of (i) chemical properties of the at least one active molecule, (ii) physical properties of the at least one active molecule, (iii) interaction of the at least one active molecule with the at least one vehicle to be designed, (iv) capacity of the at least one vehicle to be loaded with the at least one active molecule, (v) chemical and physical properties of the at least one vehicle, and (vi) a combination thereof. In an embodiment, the at least one vehicle may correspond to at least one of: a nanomaterial, a supra-biomolecule, a polymer, a hydrogel, a biodegradable material, an organic and inorganic, and combination thereof. At step 908, the designed at least one vehicle associated with the formulation on an in-silico model of a corresponding at least one chosen drug delivery route is tested to obtain a data associated with delivery of the at least one active molecule. In an embodiment, the in-silico model of the plurality of drug delivery routes may be selected from at least one of: (i) a multiscale model, (ii) an empirical relation, (iii) a physics-based model or a data-based model, (iv) a molecular model, (v) a macroscopic model, and combination thereof.

At step 910, the data associated with delivery of the at least one active molecule is reiteratively processed to obtain a desired data associated with the delivery of the at least one active molecule. In an embodiment, the desired data associated with the delivery of the at least one active molecule may correspond to at least one of: (i) a release profile of the at least active molecule, (ii) a flux of the at least one active molecule, (iii) cumulative amount of the at least one active molecule, (iv) bio-availability of the active molecule, and (v) combination thereof.

The embodiments of present disclosure herein address unresolved problem of uncertainty associated with the design of a delivery vehicle and formulation to achieve release of active molecules that meet specified targets. Usually, a large number of exploratory experiments are required to identify an appropriate vehicle and formulation for delivery of active molecules. The embodiment thus provides a generic platform for vehicle and formulation design for a given active molecule. The proposed formulation is designed with an aim to provide desired release/uptake/bioavailability of the active molecule at the site of action. Moreover, the embodiments herein further provide an integrated framework to couple multiscale, multiphysics and multi-domain modeling and simulation techniques/tools. The integrated platform provides a utility to link multiscale modelling paradigm. i.e. simulation from an electron scale to a macro scale (tablets, capsules etc.) can be performed and information from one scale to another scale can be shared/stored. The embodiments of present disclosure herein can help make informed decisions and reduce time, resource and expenses required to carry out exploratory experiments and preliminary clinical trials while designing delivery vehicles and formulations. The integrated platform provides additional feature of leveraging the knowledge databases and guiding user to make intelligent choice wherever is required. The knowledge database is also gets updated every time platform is being utilized. Thus, the integrated platform provides an end to end solution for in-silico design and testing of vehicle, formulations, and combination of both for drug delivery application.

The embodiments of present disclosure herein enable creation and application of knowledge database to filter out infeasible delivery routes for the user selected active molecule and desired release/bioavailability/uptake. The embodiments of present disclosure herein enable coupling multi-scale, multi-domain modeling and simulation techniques to aid design of delivery vehicle and formulation. The embodiments of present disclosure herein provide the knowledge database to assess feasibility of computer simulation for the given combination of the active molecule, the vehicle and formulation and the delivery route. The embodiments of present disclosure herein introduce the in-silico model of delivery routes and target sites. The embodiments of present disclosure herein configured further optimizes the design of delivery vehicle and formulation. The embodiments of present disclosure herein provide verification of stability/compatibility of the vehicle and formulation.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method of designing and testing of at least one vehicle and formulation for delivery of at least one active molecule, comprising:
receiving, via one or more hardware processors, a plurality of inputs, wherein the plurality of inputs comprises at least one of: (i) an active molecule, (ii) at least one active molecule chosen by a user from a database, and (iii) a new active molecule from at least one external database (902);
processing, via the one or more hardware processors, the plurality of inputs to determine a plurality of drug delivery routes by an action associated with the at least one active molecule (904);
designing, via the one or more hardware processors, using an integrated platform coupling modelling and simulation techniques, at least one vehicle associated with formulation based on a plurality of parameters associated with the active molecule and the plurality of drug delivery routes, wherein a plurality of material properties of the at least one vehicle and the formulation are used to arrive at transport and structural properties of the designed formulation and the designed vehicle, wherein the plurality of parameters associated with the at least one active molecule and the at least one delivery route corresponds to at least one of (i) chemical properties of the at least one active molecule, (ii) physical properties of the at least one active molecule, (iii) interaction of the at least one active molecule with the at least one vehicle to be designed, (iv) capacity of the at least one vehicle to be loaded with the at least one active molecule, (v) chemical and physical properties of the at least one vehicle, and (vi) a combination thereof, wherein the structural properties associated with the vehicle and the formulation are fed from an inbuilt information library or given as an input by the user if available or dynamically calculated and wherein the transport and structural properties includes a molecular weight, a crystallinity of a polymer, a mass of a vehicle, and a release rate of the at least one active molecule from the vehicle (906);
performing the design and an optimization loop for the at least one vehicle and the formulation until a stable and compatible vehicle and formulation combination is achieved, wherein the at least one vehicle and the formulation stability and compatibility is checked with the modelling and simulation techniques, wherein the optimization loop changes or adapts the material properties of at least one vehicle and the formulation while assessing feasibility of synthesis of the at least one vehicle and the formulation, wherein the optimization loop takes an information from a knowledge database, and provides the information to the knowledge database at every instance pertaining to the optimized vehicle and formulation for the at least one active molecule and at least one drug delivery route, wherein the knowledge database includes a model feasibility information and is updated at every instance if the integrated platform is executed, and wherein the model feasibility information decides whether it is computationally feasible to carry out in-silico simulation in stipulated amount of time;
testing, via the one or more hardware processors, the designed at least one vehicle associated with the formulation on an in-silico model of a corresponding at least one chosen drug delivery route to obtain a data associated with delivery of the at least one active molecule, wherein the testing comprises performing the in-silico simulation on the in-silico model of the delivery route and targeting organ and/or tissue for the at least one drug delivery route and estimates release, bioavailability, uptake, toxicity of the active molecule, wherein the at least one of the formulation, the vehicle, and combination thereof are screened based on the release through the in-silico model, uptake in the in-silico model, bioavailability inside the in-silico model and toxicity (908); and reiteratively processing, via the one or more hardware processors, the data associated with delivery of the at least one active molecule to obtain a desired data associated with the delivery of the at least one active molecule (910).

2. The processor implemented method as claimed in claim 1, wherein the at least one active molecule corresponds to a drug molecule.

3. The processor implemented method as claimed in claim 1, wherein the action associated with the at least one active molecule is tuned to a plurality of responses, wherein the plurality of responses corresponds to at least one of: (i) an instantaneous, (ii) a controlled, (iii) an extended, (iv) a personalized, (v) a pulsatile, and (vi) a desired response for the active molecule.

4. The processor implemented method as claimed in claim 1, wherein the at least one vehicle corresponds to at least one of: a nanomaterial, a supra-biomolecule, a polymer, a hydrogel, a biodegradable material, an organic and inorganic, and combination thereof.

5. The processor implemented method as claimed in claim 1, wherein the in-silico model of the plurality of drug delivery routes is selected from at least one of: (i) a multiscale model, (ii) an empirical relation, (iii) a physics-based model or a data-based model, (iv) a molecular model, (v) a macroscopic model, and combination thereof.

6. The processor implemented method as claimed in claim 1, wherein the desired data associated with the delivery of the at least one active molecule corresponds to at least one of: (i) a release profile of the at least active molecule, (ii) a flux of the at least one active molecule, (iii) cumulative amount of the at least one active molecule, (iv) bio-availability of the active molecule, and (v) combination thereof.

7. A system (100) to design and test at least one vehicle and formulation for delivery of at least one active molecule, comprising:

a memory (102) storing instructions;

one or more communication interfaces (106); and one or more hardware processors (104) coupled to the memory (102) via the one or more communication interfaces (106), wherein the one or more hardware processors (104) are configured by the instructions to:

receive, a plurality of inputs, wherein the plurality of inputs comprises at least one of: (i) an active molecule, (ii) at least one active molecule chosen by a user from a database, and (iii) a new active molecule from at least one external database;

process, the plurality of inputs to determine a plurality of drug delivery routes by an action associated with the at least one active molecule;

design, using an integrated platform coupling modelling and simulation techniques, at least one vehicle associated with formulation based on a plurality of parameters associated with the active molecule and the plurality of drug delivery routes, wherein a plurality of material properties of the at least one vehicle and the formulation are used to arrive at transport and structural properties of the designed formulation and the designed vehicle, wherein the plurality of parameters associated with the at least one active molecule and the at least one delivery route corresponds to at least one of (i) chemical properties of the at least one active molecule, (ii) physical properties of the at least one active molecule, (iii) interaction of the at least one active molecule with the at least one vehicle to be designed, (iv) capacity of the at least one vehicle to be loaded with the at least one active molecule, (v) chemical and physical properties of the at least one vehicle, and (vi) a combination thereof, wherein the structural properties associated with the vehicle and the formulation are fed from an inbuilt information library or given as an input by the user if available or dynamically calculated and wherein the transport and structural properties includes a molecular weight, a crystallinity of a polymer, a mass of a vehicle, and a release rate of the at least one active molecule from the vehicle;

perform, the design and an optimization loop for the at least one vehicle and the formulation until a stable and compatible vehicle and formulation combination is achieved, wherein the at least one vehicle and the formulation stability and compatibility is checked with the modelling and simulation techniques, wherein the optimization loop changes or adapts the material properties of at least one vehicle and the formulation while assessing feasibility of synthesis of the at least one vehicle and the formulation, wherein the optimization loop takes an information from a knowledge database, and provides the information to the knowledge database at every instance pertaining to the optimized vehicle and formulation for the at least one active molecule and at least one drug delivery route, wherein the knowledge database includes a model feasibility information and is updated at every instance if the integrated platform is executed, and wherein the model feasibility information decides whether it is computationally feasible to carry out in-silico simulation in stipulated amount of time;

test, the designed at least one vehicle associated with the formulation on an in-silico model of a corresponding at least one chosen drug delivery route to obtain a data associated with delivery of the at least one active molecule, wherein the testing comprises performing the in-silico simulation on the in-silico model of the delivery route and targeting organ and/or tissue for the at least one drug delivery route and estimates release, bioavailability, uptake, toxicity of the active molecule, wherein the at least one of the formulation, the vehicle, and combination thereof are screened based on the release through the in-silico model, uptake in the in-silico model, bioavailability inside the in-silico model and toxicity; and reiteratively process, the data associated with delivery of the at least one active molecule to obtain a desired data associated with the delivery of the at least one active molecule.

8. The system as claimed in claim 7, wherein the at least one active molecule corresponds to a drug molecule.

9. The system as claimed in claim 7, wherein the action associated with the at least one active molecule is tuned to a plurality of responses, wherein the plurality of responses corresponds to at least one of: (i) an instantaneous, (ii) a controlled, (iii) an extended, (iv) a personalized, (v) a pulsatile, and (vi) a desired response for the active molecule.

10. The system as claimed in claim 7, wherein the at least one vehicle corresponds to at least one of: a nanomaterial, a supra-biomolecule, a polymer, a hydrogel, a biodegradable material, an organic and inorganic, and combination thereof.

11. The system as claimed in claim 7, wherein the in-silico model of the plurality of drug delivery routes is selected from at least one of: (i) a multiscale model, (ii) an empirical relation, (iii) a physics-based model or a data-based model, (iv) a molecular model, (v) a macroscopic model, and combination thereof.

12. The system as claimed in claim 7, wherein the desired data associated with the delivery of the at least one active molecule corresponds to at least one of: (i) a release profile of the at least active molecule, (ii) a flux of the at least one active molecule, (iii) cumulative amount of the at least one active molecule, (iv) bio-availability of the active molecule, and (v) combination thereof.

* * * * *